United States Patent
Smith et al.

(10) Patent No.: US 8,006,692 B2
(45) Date of Patent: Aug. 30, 2011

(54) GAS BLENDER WITH AUXILIARY MIXED GAS OUTLET

(75) Inventors: Michael S. Smith, Lake Arrowhead, CA (US); Greg Voss, Lakeville, MN (US); Peter Bliss, Prior Lake, MN (US); Scott Halperin, Orange, CA (US)

(73) Assignee: CareFusion 2200, Inc., San Diego, CA (US)

( * ) Notice: Subject to any disclaimer, the term of this patent is extended or adjusted under 35 U.S.C. 154(b) by 1519 days.

(21) Appl. No.: 11/292,641

(22) Filed: Dec. 2, 2005

(65) Prior Publication Data
US 2007/0125374 A1 Jun. 7, 2007

(51) Int. Cl.
*A61M 15/00* (2006.01)
(52) U.S. Cl. .......... 128/203.12; 128/203.14; 128/203.25
(58) Field of Classification Search .......... 128/203.12–203.14, 203.22–203.26, 128/203.18
See application file for complete search history.

(56) References Cited

U.S. PATENT DOCUMENTS
| | | | |
|---|---|---|---|
| 5,014,694 A | 5/1991 | DeVries | |
| 5,878,771 A | 3/1999 | Mayeaux | |
| 6,467,478 B1 | 10/2002 | Merrick et al. | |
| 2004/0040437 A1 | 3/2004 | Cao et al. | |

FOREIGN PATENT DOCUMENTS
| | | |
|---|---|---|
| RU | 2080884 C1 | 6/1997 |
| WO | 9521406 | 8/1995 |
| WO | WO 2004/032727 A2 * | 4/2007 |

OTHER PUBLICATIONS
PCT Search Report mailed Sep. 26, 2007; 10 pgs.
Russian Decision on Grant issued Nov. 29, 2010 (17 pages).

* cited by examiner

*Primary Examiner* — Patricia M Bianco
*Assistant Examiner* — Camtu T Nguyen
(74) *Attorney, Agent, or Firm* — Dicke, Billig & Czaja, PLLC

(57) ABSTRACT

A gas blender with auxiliary mixed gas outlet for mixing a primary gas, generally air, and a secondary gas, generally oxygen, to obtain a mixed gas having several controlled characteristics. The gas blender may be incorporated into a Continuous Positive Airway Pressure (CPAP) device. The gas blender controls the mixing to produce the mixed gas having a predetermined mixture setpoint, generally an oxygen percentage, and a predetermined control setpoint, generally a pressure setpoint or flow rate setpoint. The gas blender provides an auxiliary mixed gas source for use by an auxiliary piece of equipment such as a nebulizer or resuscitation bag. The gas blender includes a primary gas inlet passageway, a secondary gas inlet passageway, a gas mixing apparatus, a mixed gas distribution passageway with an auxiliary mixed gas outlet, a gas sensor, a delivery sensor, a mixed gas delivery control valve, a mixed gas controlled passageway, and a controller.

35 Claims, 7 Drawing Sheets

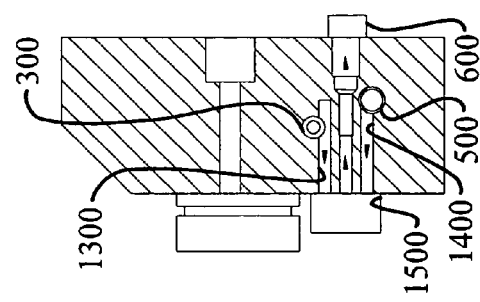
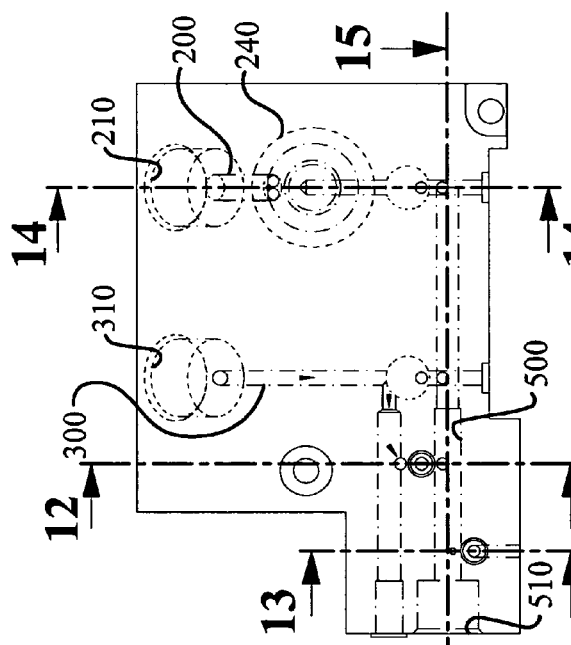
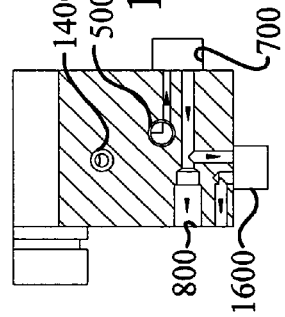
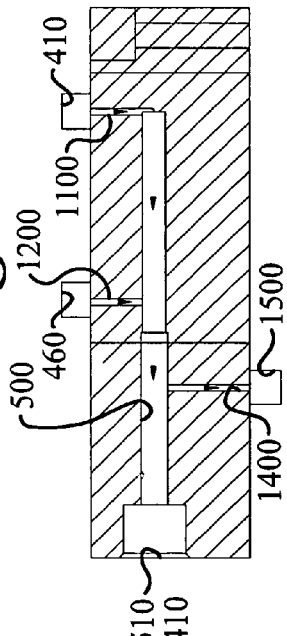
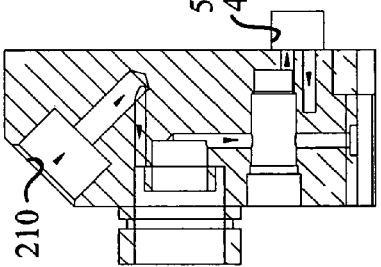

GAS BLENDER WITH AUXILIARY MIXED GAS OUTLET

TECHNICAL FIELD

The present invention generally relates to a gas mixing and control device, especially for a gas blending device particularly suited for supplying mixed gas to a Continuous Positive Airway Pressure (CPAP) medical device.

BACKGROUND OF THE INVENTION

Oxygen therapy is used to treat patients suffering from a wide variety of ailments and to assist in numerous treatments. One of the most important aspects of such therapy is obtaining the correct oxygen mixture and pressure of the treatment gas. A common form of oxygen therapy is accomplished through the use of a Continuous Positive Airway Pressure (CPAP) device. As those skilled in oxygen therapy will recognize, numerous other auxiliary therapy devices that require mixed gas are used in conjunction with CPAP therapy. Such auxiliary devices include nebulizers and resuscitation bags.

Medical compressed air and oxygen are mixed, or blended, to obtain the correct oxygen mixture and pressure of the treatment, or mixed, gas. While many oxygen therapy devices have the ability to properly mix the medical compressed air and oxygen built into the device, several devices do not, and require connection to an external gas blender so that the device is supplied with pre-mixed gas. The devices that incorporate the gas mixing capability include a gas blender. A gas blender is a device that properly mixes the medical compressed air and the oxygen to obtain a mixed gas with a specific oxygen percentage and pressure. It is desirable to have an integral gas blender that includes an auxiliary mixed gas outlet that can be used to supply mixed gas to equipment that does not have a built-in blender. Incorporation of such an auxiliary mixed gas outlet eliminates the need for an external gas blender for many pieces of equipment.

Presently a limited number of commercially available devices incorporate an auxiliary mixed gas outlet, but these devices have a number of drawbacks. First, it is believed that the presently available gas blenders having an auxiliary gas outlet can only supply mixed air via a treatment outlet or the auxiliary outlet, not both outlets at the same time. Secondly, presently available auxiliary gas outlets often can only supply mixed gas at low flow rates, thereby limiting the types of auxiliary equipment that can be supplied with the mixed gas from the auxiliary gas outlet.

The art needs a gas blender that can supply mixed air to a treatment outlet and an auxiliary gas outlet at the same time. Further, a gas blender that automatically adjusts during use of the auxiliary gas outlet so as not to affect the mixed gas flow from the treatment outlet is desirable. Additionally, an ideal gas blender will not unduly restrict the flow out of the auxiliary gas outlet.

SUMMARY OF THE INVENTION

In its most general configuration, the present invention advances the state of the art with a variety of new capabilities and overcomes many of the shortcomings of prior devices in new and novel ways. In its most general sense, the present invention overcomes the shortcomings and limitations of the prior art in any of a number of generally effective configurations. The instant invention demonstrates such capabilities and overcomes many of the shortcomings of prior methods in new and novel ways.

The instant invention is a gas blender with auxiliary mixed gas outlet. The gas blender mixes a primary gas and a secondary gas in a particular fashion to obtain a mixed gas having several controlled characteristics. The gas blender of the present invention may be incorporated into a Continuous Positive Airway Pressure (CPAP) device. In such an embodiment the primary gas is generally medical compressed air and the secondary gas is oxygen.

The primary gas enters the gas blender at a primary gas source pressure and the secondary gas enters the gas blender at a secondary gas source pressure. While the gases may be any gases, and the source pressures may be any pressure, in the healthcare industry the gases are most commonly air and oxygen, and the source pressures are most commonly between 40-66 psig. The gas blender controls the mixing to produce the mixed gas having a predetermined mixture setpoint, generally an oxygen percentage, and a predetermined control setpoint, generally a pressure setpoint or flow rate setpoint.

The gas blender provides an auxiliary mixed gas source at a pressure of at least fifty percent of either gas for selective use by an auxiliary piece of equipment. With reference again to the healthcare industry, the at least one auxiliary piece of equipment that uses the mixed gas at a pressure of at least fifty percent of the source pressure is most commonly, nebulizers, resuscitation bags, or the like.

The gas blender includes a primary gas inlet passageway, a secondary gas inlet passageway, a gas mixing apparatus, a mixed gas distribution passageway with an auxiliary mixed gas outlet, a gas sensor, a delivery sensor, a mixed gas delivery control valve, a mixed gas controlled passageway, and a controller.

The primary gas inlet passageway has a primary gas inlet port, for receiving the primary gas from an external source, and a primary gas inlet passageway discharge. The secondary gas inlet passageway has a secondary gas inlet port, for receiving the secondary gas from an external source, and a secondary gas inlet passageway discharge. The mixed gas distribution passageway has the auxiliary mixed gas outlet for supplying the mixed gas at the predetermined mixture setpoint and a pressure of at least fifty percent of the primary gas source pressure for use by the auxiliary piece of equipment. Lastly, the mixed gas controlled passageway has a mixed gas controlled passageway inlet and a mixed gas controlled passageway discharge.

The gas mixing apparatus is in fluid communication with the primary gas inlet passageway, the secondary gas inlet passageway, and the mixed gas distribution passageway. The gas mixing apparatus receives primary gas through the primary gas inlet passageway and receives secondary gas through the secondary gas inlet passageway. The gas mixing apparatus mixes the primary gas with the secondary gas in response to a mixing control signal to produce the mixed gas at the predetermined mixture setpoint and a pressure of at least fifty percent of the primary gas source pressure.

The predetermined mixture setpoint is a percentage of either the primary gas or the secondary gas that is desired in the mixed gas. The mixed gas then exits the gas mixing apparatus via the mixed gas distribution passageway. The mixed gas distribution passageway of the present invention has an auxiliary mixed gas outlet for supplying mixed gas at the predetermined mixture setpoint and a pressure of at least fifty percent of the primary gas source pressure, for use by the auxiliary piece of equipment. This ability to supply mixed gas at a pressure of at least fifty percent of the source pressure of the primary gas and the secondary gas, while also supplying mixed gas via another outlet at a reduced pressure or flow, is a significant advance.

The mixed gas delivery control valve is in fluid communication with the mixed gas distribution passageway and a mixed gas controlled passageway. The mixed gas delivery control valve receives the mixed gas downstream of the gas mixing apparatus and therefore the mixed gas is at the predetermined mixture setpoint. The mixed gas delivery control valve modulates in response to a delivery control signal, thereby fixing the mixed gas at the predetermined control setpoint, in addition to the already obtained predetermined mixture setpoint. The mixed gas, now at the predetermined mixture setpoint and predetermined control setpoint, exits the mixed gas delivery control valve via the mixed gas passageway.

The gas sensor is in fluid communication with the mixed gas distribution passageway. The gas sensor produces a gas signal representative of a property of the mixed gas in the mixed gas distribution passageway. The gas sensor generally senses the amount of the first gas or the second gas contained in the mixed gas. The sensed amount is preferably in the form of a percentage of the first gas or the second gas contained in the mixed gas.

The delivery sensor is in fluid communication with the mixed gas after it exits the mixed gas delivery control valve for generating a delivery sensing signal. At this point the mixed gas is already at the desired mixture, and the delivery sensor is sensing pressure or flow rate.

Finally, the controller (a) compares the predetermined mixture setpoint and the gas signal, and generates the mixing control signal, and (b) compares the predetermined control setpoint and the delivery sensing signal, and generates the delivery control signal. In other words, the controller receives the user input, or preset, predetermined mixture setpoint as well as the gas signal from the gas sensor, compares the signals, and generates a correction signal, or mixing control signal, that modulates the gas mixing apparatus to ensure that the mixed gas in the mixed gas distribution passageway is substantially equal to the mixture amount represented by the predetermined mixture setpoint. Further, the controller receives the user input, or preset, predetermined control setpoint as well as the delivery sensing signal from the delivery sensor, compares the signals, and generates a correction signal, or delivery control signal. The delivery control signal modulates the mixed gas delivery control valve to ensure that a characteristic, typically pressure or flow rate, of the mixed gas in the mixed gas controlled passageway is substantially equal to the characteristic, typically pressure or flow rate, represented by the predetermined control setpoint.

The present invention may also incorporate a calibration valve (1500) to control which gas (10, 20, 30) is sensed by the gas sensor (600); a mixed gas vent valve (1600) in fluid communication with the mixed gas controlled passageway (800); a relief valve (1700) in fluid communication with the mixed gas controlled passageway (800); and various inlet and outlet check valves.

These variations, modifications, alternatives, and alterations of the various preferred embodiments, arrangements, and configurations may be used alone or in combination with one another as will become more readily apparent to those with skill in the art, with reference to the following detailed description of the preferred embodiments and the accompanying figures and drawings.

BRIEF DESCRIPTION OF THE DRAWINGS

Without limiting the scope of the present invention as claimed below and referring now to the drawings and figures:

FIG. 11 is a top plan view of the present invention, not to scale;
FIG. 12 is a sectional view of the present invention taken along section line 12-12 in FIG. 11, not to scale;
FIG. 13 is a sectional view of the present invention taken along section line 13-13 in FIG. 11, not to scale;
FIG. 14 is a sectional view of the present invention taken along section line 14-14 in FIG. 11, not to scale;
and
FIG. 15 is a sectional view of the present invention taken along section line 15-15 in FIG. 11, not to scale.

DETAILED DESCRIPTION OF THE INVENTION

Figure 1:
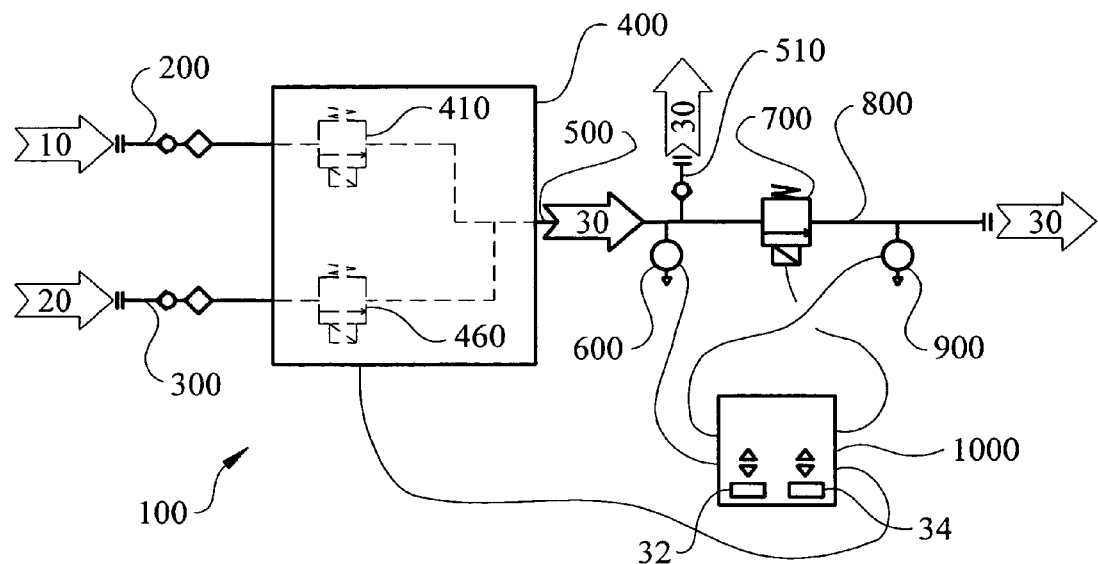
FIG. 1 is a schematic of the present invention, not to scale.

The gas blender with auxiliary mixed gas outlet (100) of the instant invention enables a significant advance in the state of the art. The preferred embodiments of the apparatus accomplish this by new and novel arrangements of elements that are configured in unique and novel ways and which demonstrate previously unavailable but preferred and desirable capabilities. The detailed description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

Referring generally to FIGS. 1 through 15, the instant invention is a gas blender with auxiliary mixed gas outlet (100) for mixing a primary gas (10) and a secondary gas (20) in a particular fashion to obtain a mixed gas (30) having several controlled characteristics. The primary gas (10) enters the gas blender (100) at a primary gas source pressure and the secondary gas (20) enters the gas blender (100) at a secondary gas source pressure. While the gases (10, 20) may be any gases, and the source pressures may be any pressure, in the healthcare industry the gases (10, 20) are most commonly air and oxygen, and the source pressures are most commonly between 40-66 psig (2.75-4.55 bar). The gas blender (100) controls the mixing to produce the mixed gas (30) having a predetermined mixture setpoint (32) and a predetermined control setpoint (34). Further, the gas blender (100) provides an auxiliary mixed gas (30) source at a pressure of at least fifty percent of either gas (10, 20) for selective use by at least one auxiliary piece of equipment. With reference again to the healthcare industry, the at least one auxiliary piece of equipment that uses the mixed gas (30) at a pressure of at least fifty percent of the source pressure is most commonly, nebulizers, resuscitation bags, or the like.

With reference to FIG. 1, the gas blender (100) includes a primary gas inlet passageway (200), a secondary gas inlet passageway (300), a gas mixing apparatus (400), a mixed gas distribution passageway (500) with an auxiliary mixed gas outlet (510), a gas sensor (600), a delivery sensor (900), a mixed gas delivery control valve (700), a mixed gas controlled passageway (800), and a controller (1000). Each of these elements will be first briefly discussed to provide an overview of the fluid communication among the various elements and how the gas blender (100) functions.

Figure 2:
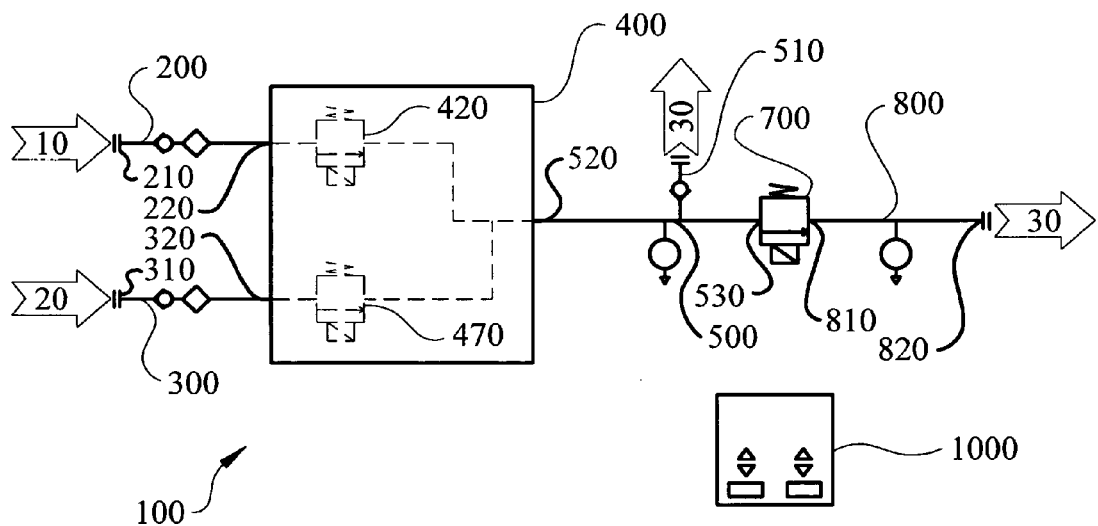
FIG. 2 is a schematic of the present invention, not to scale.

First, with respect the passageways (200, 300, 500, 800), as seen in FIG. 2, the primary gas inlet passageway (200) has a primary gas inlet port (210), for receiving the primary gas (10) from an external source, and a primary gas inlet passageway discharge (220). Similarly, the secondary gas inlet passageway (300) has a secondary gas inlet port (310), for receiving the secondary gas (20) from an external source, and a secondary gas inlet passageway discharge (320). Further, the mixed gas distribution passageway (500) has the auxiliary mixed gas outlet (510) for supplying the mixed gas (30) at the predetermined mixture setpoint (32) and a pressure of at least fifty percent of the primary gas source pressure for use by the auxiliary piece of equipment. The mixed gas distribution passageway (500) also has a mixed gas distribution passageway inlet (520) and a mixed gas distribution passageway discharge (530). Lastly, the mixed gas controlled passageway (800) has a mixed gas controlled passageway inlet (810) and a mixed gas controlled passageway discharge (820).

Figure 3:
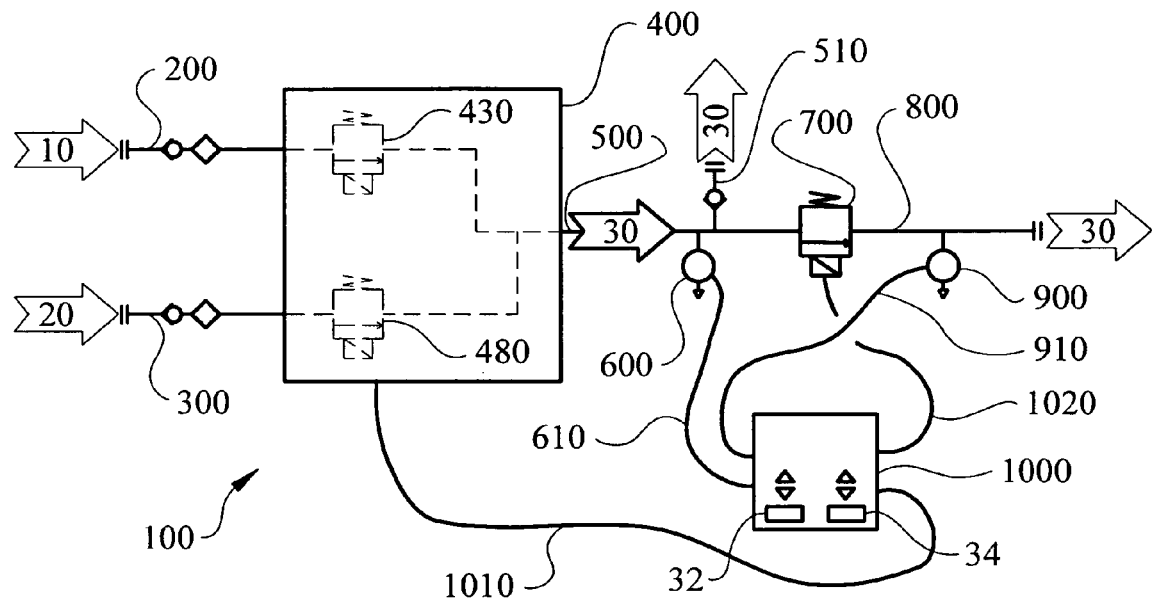
FIG. 3 is a schematic of the present invention, not to scale.

Next, with continued reference to FIG. 2, the gas mixing apparatus (400) is in fluid communication with the primary gas inlet passageway (200), the secondary gas inlet passageway (300), and the mixed gas distribution passageway (500). The gas mixing apparatus (400) receives primary gas (10) through the primary gas inlet passageway (200) and receives secondary gas (20) through the secondary gas inlet passageway (300). The gas mixing apparatus (400) mixes the primary gas (10) with the secondary gas (20) in response to a mixing control signal (1010) to produce the mixed gas (30) at the predetermined mixture setpoint (32) and a pressure of at least fifty percent of the primary gas source pressure, as seen in FIG. 3. The predetermined mixture setpoint (32) is a percentage of either the primary gas (10) or the secondary gas (20) that is desired in the mixed gas (30). The mixed gas (30) then exits the gas mixing apparatus (400) via the mixed gas distribution passageway (500). The mixed gas distribution passageway (500) of the present invention has an auxiliary mixed gas outlet (510) for supplying mixed gas (30) at the predetermined mixture setpoint (32) and a pressure of at least fifty percent of the primary gas source pressure for use by the auxiliary piece of equipment. This ability to supply mixed gas (30) at a pressure of at least fifty percent of the source pressure of the primary gas (10) and the secondary gas (20), while also supplying mixed gas (30) via another outlet at a reduced pressure or flow, is a significant advance.

Again referring to FIG. 2, the mixed gas delivery control valve (700) is in fluid communication with the mixed gas distribution passageway (500) and a mixed gas controlled passageway (800). The mixed gas delivery control valve (700) receives the mixed gas (30) downstream of the gas mixing apparatus (400) and therefore the mixed gas (30) is at the predetermined mixture setpoint (32). The mixed gas delivery control valve (700) modulates in response to a delivery control signal (1020) thereby fixing the mixed gas (30) at the predetermined control setpoint (34), in addition to the already obtained predetermined mixture setpoint (32). The mixed gas (30), now at the predetermined mixture setpoint (32) and predetermined control setpoint (34), exits the mixed gas delivery control valve (700) via the mixed gas controlled passageway (800).

Now, referring again to FIG. 3, with respect to the sensors (600, 900), the gas sensor (600) is in fluid communication with the mixed gas distribution passageway (500). The gas sensor (600) produces a gas signal (610) representative of a property of the mixed gas (30) in the mixed gas distribution passageway (500). The gas sensor (600) generally senses the amount of the first gas (10) or the second gas (20) contained in the mixed gas (30). The sensed amount is preferably in the form of a percentage of the first gas (10) or the second gas (20) contained in the mixed gas (30). For example, in the healthcare industry if the first gas (10) is compressed air and the second gas (20) is substantially pure oxygen, then it is generally desirable to sense the amount of oxygen in the mixed gas (30), often expressed as a percentage of oxygen in the mixed gas (30).

The delivery sensor (900) is in fluid communication with the mixed gas (30) after it exits the mixed gas delivery control valve (700) for generating a delivery sensing signal (910). At this point the mixed gas (30) is already at the desired mixture, and the delivery sensor (900) is sensing pressure or flow rate. Thus, the delivery sensor may be a pressure sensor (920) or a flow sensor (930). Further, the delivery sensor (900) is not restricted to locations within the present invention and may be in fluid communication with the mixed gas (30) well downstream of the gas blender (100). For instance, referring again to a healthcare example, in embodiments using the present invention in a Continuous Positive Airway Pressure (CPAP) device, the mixed gas (30) pressure is preferably measured with the pressure sensor (920) or flow sensor (930) located near a user face mask. In most embodiments the pressure sensor (920) is sensing pressures below 250 centimeters of water, and the flow sensor (930) is sensing flow rates less than 20 liters per minute.

Finally, the controller (1000) (a) compares the predetermined mixture setpoint (32) and the gas signal (610), and generates the mixing control signal (1010), and (b) compares the predetermined control setpoint (34) and the delivery sensing signal (910), and generates the delivery control signal (1020). In other words, with respect to the mixing control signal (1010), the controller (1000) receives the user input, or preset, predetermined mixture setpoint (32) as well as the gas signal (610) from the gas sensor (600), compares the signals, and generates a correction signal, or mixing control signal (1010), that modulates the gas mixing apparatus (400) to ensure that the mixed gas (30) in the mixed gas distribution passageway (500) is substantially equal to the mixture amount represented by the predetermined mixture setpoint (32). Further, with respect to the delivery control signal (1020), the controller (1000) receives the user input, or preset, predetermined control setpoint (34) as well as the delivery sensing signal (910) from the delivery sensor (900), compares the signals, and generates a correction signal, or delivery control signal (1020), that modulates the mixed gas delivery control valve (700) to ensure that a characteristic, typically pressure or flow rate, of the mixed gas (30) in the mixed gas controlled passageway (800) is substantially equal to the characteristic, typically pressure or flow rate, represented by the predetermined control setpoint (34).

The gas mixing apparatus (400) may be any number of flow control products that can accurately meter the amount of gas passing through the apparatus (400) and mix the primary gas (10) and the secondary gas (20) with a known maximum pressure drop to ensure that the mixed gas (30) in the mixed gas distribution passageway (500) is at a pressure of at least fifty percent of the source pressure of the primary gas (30). In one embodiment, seen in FIG. 1, the gas mixing apparatus (400) includes a primary gas control valve (410) and a secondary gas control valve (460). The term control valve used herein means a valve and compatible actuation device capable of responding to the associated control signal to modulate, or merely direct the flow, as directed by the control signal. In a preferred embodiment, seen in FIG. 2, the primary gas control valve (410) is a primary gas proportional solenoid valve (420) and the secondary gas control valve (460) is a secondary gas proportional solenoid valve (470). The term proportional solenoid valve herein means a solenoid valve capable of modulating through the range of being fully open to fully closed.

Figure 4:
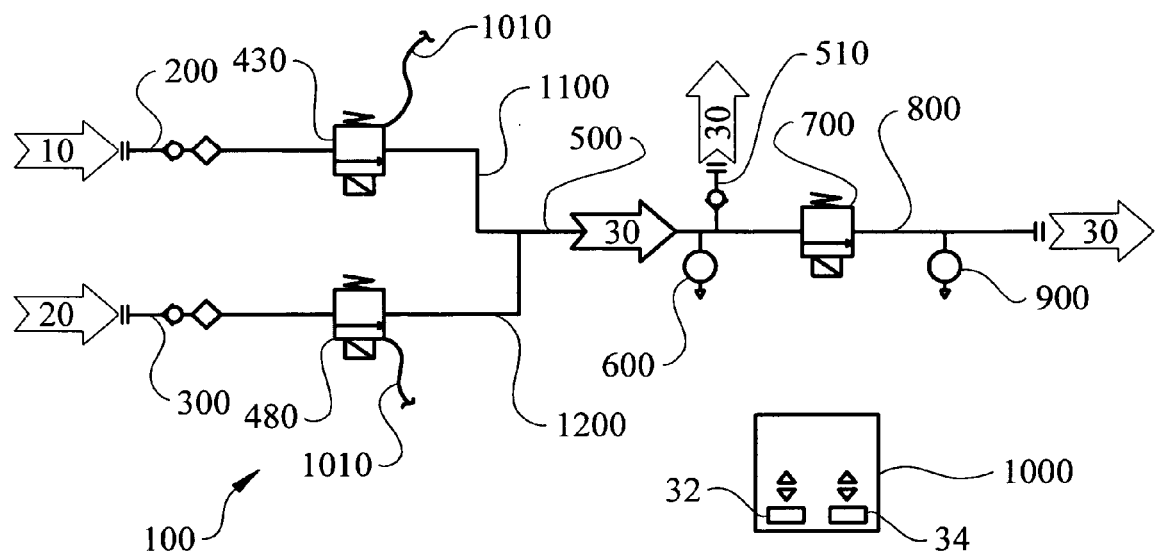
FIG. 4 is a schematic of the present invention, not to scale.

In one particular embodiment, seen in FIGS. 3 and 4, the primary gas proportional solenoid valve (420) is a 2-way primary gas proportional solenoid valve (430) and the secondary gas proportional solenoid valve (470) is a 2-way secondary gas proportional solenoid valve (480). Here, the 2-way primary gas proportional solenoid valve (430) is in fluid communication with the primary gas inlet passageway (200) and a primary gas controlled passageway (1100) such that the 2-way primary gas proportional solenoid valve (430) received the primary gas (10) from the primary gas inlet passageway (200), modulates in response to the mixing control signal (1010), and discharges the modulated primary gas (10) to the primary gas controlled passageway (1100) that is in fluid communication with the mixed gas distribution passageway (500). Similarly, the 2-way secondary gas proportional solenoid valve (480) is in fluid communication with the secondary gas inlet passageway (300) and a secondary gas controlled passageway (1200) such that the 2-way secondary gas proportional solenoid valve (480) receives the secondary gas (20) from the secondary gas inlet passageway (300), modulates in response to the mixing control signal (1010), and discharges the modulated secondary gas (20) to the secondary gas controlled passageway (1200) that is in fluid communication with the mixed gas distribution passageway (500). The 2-way primary gas proportional solenoid valve (430) and the 2-way secondary gas proportional solenoid valve (480) work together, as directed by the mixing control signal (1010), so that the mixture of the modulated primary gas (10) and the modulated secondary gas (20) in the mixed gas distribution passageway (500) is at the predetermined mixture setpoint (32).

In this embodiment incorporated into an illustrative CPAP application example, the predetermined control setpoint (34) is often a preferred treatment pressure of between approximately 5 centimeters of water and approximately 10 centimeters of water, with the source pressure of the first gas (10), compressed air, of approximately 50 psig (3.45 bar) and the source pressure of the second gas (20), oxygen, of approximately 50 psig, when the mixed gas (30) flow out of the auxiliary mixed gas outlet (510) is approximately 7 liters/minute and the mixed gas (30) flow out of the mixed gas controlled passageway (800) is approximately 8 liters/minute. As the mixed gas (30) flow from the auxiliary mixed gas outlet (510) increases to 15 liters/minute the source pressure of the gases (10, 20) drops to approximately 41 psig. The higher flow rate yields a pressure in the mixed gas distribution passageway (500) of approximately 21 psig, while the lower flow rate yields a pressure in the mixed gas distribution passageway (500) of approximately 42 psig. As such, the mixed gas (30) in the mixed gas distribution passageway (500) is at the predetermined mixture setpoint (32) and a pressure of at least fifty percent of the lowest gas source pressure. Similarly, in the CPAP application example above, the predetermined control setpoint (34) is often a preferred treatment flow rate of less than 20 liters per minute.

Figure 5:
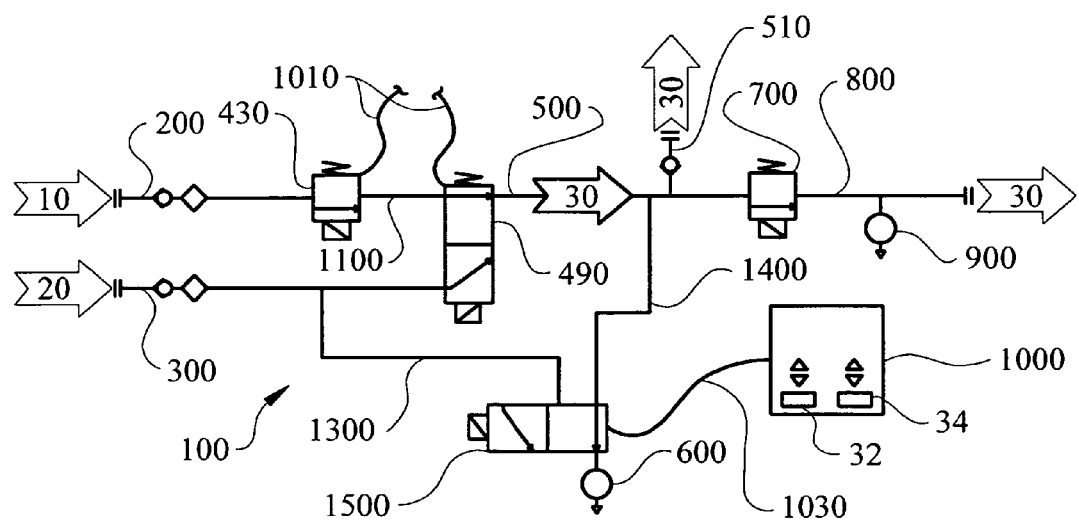
FIG. 5 is a schematic of the present invention, not to scale.
Figure 6:
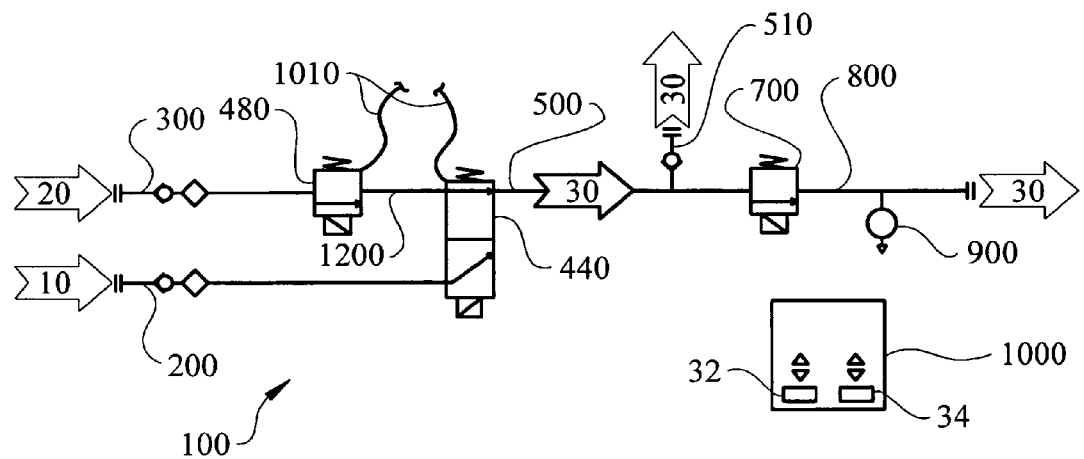
FIG. 6 is a schematic of the present invention, not to scale.

In an alternative embodiment seen in FIG. 5, the primary gas proportional solenoid valve (420) is a 2-way primary gas proportional solenoid valve (430) and the secondary gas proportional solenoid valve (470) is a 3-way secondary gas proportional solenoid valve (490). Here, the 2-way primary gas proportional solenoid valve (430) is in fluid communication with the primary gas inlet passageway (200) and a primary gas controlled passageway (1100) such that the 2-way primary gas proportional solenoid valve (430) receives the primary gas (10) from the primary gas inlet passageway (200) and modulates in response to the mixing control signal (1010) only when the predetermined mixture setpoint (32) is at or above a predetermined high concentration setpoint (36). When the predetermined mixture setpoint (32) is below the predetermined high concentration setpoint (36) the 2-way primary gas proportional solenoid valve (430) is fully open. The discharge from the 2-way primary gas proportional solenoid valve (430) of this embodiment is to the primary gas controlled passageway (1100) that is in fluid communication with the 3-way secondary gas proportional solenoid valve (490). Therefore, the 3-way secondary gas proportional solenoid valve (490) is in fluid communication with the secondary gas inlet passageway (300), the primary gas controlled passageway (1100), and the mixed gas distribution passageway (500) such that the 3-way secondary gas proportional solenoid valve (430) receives the secondary gas (20) from the secondary gas inlet passageway (300) and receives the primary gas (10) from the primary gas controlled passageway (1100). The 3-way secondary gas proportional solenoid valve (490) modulates in response to the mixing control signal (1010), and discharges the mixed gas (30) to the mixed gas distribution passageway (500) at the predetermined mixture setpoint (32).

In this embodiment the predetermined high concentration setpoint (36) can be virtually any concentration of the primary gas (10) or the secondary gas (20). With reference again to a healthcare example in which the primary gas (10) is compressed air and the secondary gas (20) is oxygen, the predetermined high concentration setpoint (36) of the mixed gas (30) is substantially sixty percent oxygen. This value is selected because given an equal volume transfer, assuming the same source pressure of each gas (10, 20) and equal orifice sizes of each valve (410, 460), the compressed air, at 21% oxygen, and oxygen, at 100% oxygen, would mix in equal parts. Here, the difference in the percentage of oxygen in the primary gas (10) and the secondary gas (20) is approximately 80%. Thus, with the 2-way primary gas proportional solenoid valve (430) fully open, the 3-way secondary gas proportional solenoid valve (490) can modulate to produced the mixed gas (30) having oxygen concentrations of between 21% and approximately 60% by volume. Then, if an oxygen concentration greater than 60% is desired, the 2-way primary gas proportional solenoid valve (430) starts to close, or throttle back the amount of the secondary gas (20), i.e. compressed air, that it supplies to the 3-way secondary gas proportional solenoid valve (490).

One with skill in the art will recognize that an embodiment that is exactly the inverse of the previously described embodiment of FIG. 5 will perform equally as well. In this inverse embodiment, seen in FIG. 6, the primary gas proportional solenoid valve (420) is a 3-way primary gas proportional solenoid valve (440) and the secondary gas proportional solenoid valve (470) is a 2-way secondary gas proportional solenoid valve (480). The 2-way secondary gas proportional solenoid valve (480) is in fluid communication with the secondary gas inlet passageway (300) and a secondary gas controlled passageway (1200). The 2-way secondary gas proportional solenoid valve (480) receives the secondary gas (20) from the secondary gas inlet passageway (300), modulates in response to the mixing control signal (1010) only when the predetermined mixture setpoint (32) is at or above a predetermined high concentration setpoint (36), otherwise the 2-way secondary gas proportional solenoid valve (480) is fully open, and discharges the secondary gas (20) to the secondary gas controlled passageway (1200). The secondary gas controlled passageway (1200) is in fluid communication with the 3-way primary gas proportional solenoid valve (440). The 3-way primary gas proportional solenoid valve (440) is in fluid communication with the primary gas inlet passageway (200), the secondary gas controlled passageway (1200), and the mixed gas distribution passageway (500). The 3-way primary gas proportional solenoid valve (440) receives the primary gas (10) from the primary gas inlet passageway (200) and receives the secondary gas (20) from the secondary gas controlled passageway (1200). The 3-way primary gas proportional solenoid valve (440) modulates in response to the mixing control signal (1010) and discharges the mixed gas (30) to the mixed gas distribution passageway (500) at the predetermined mixture setpoint (32).

Figure 7:
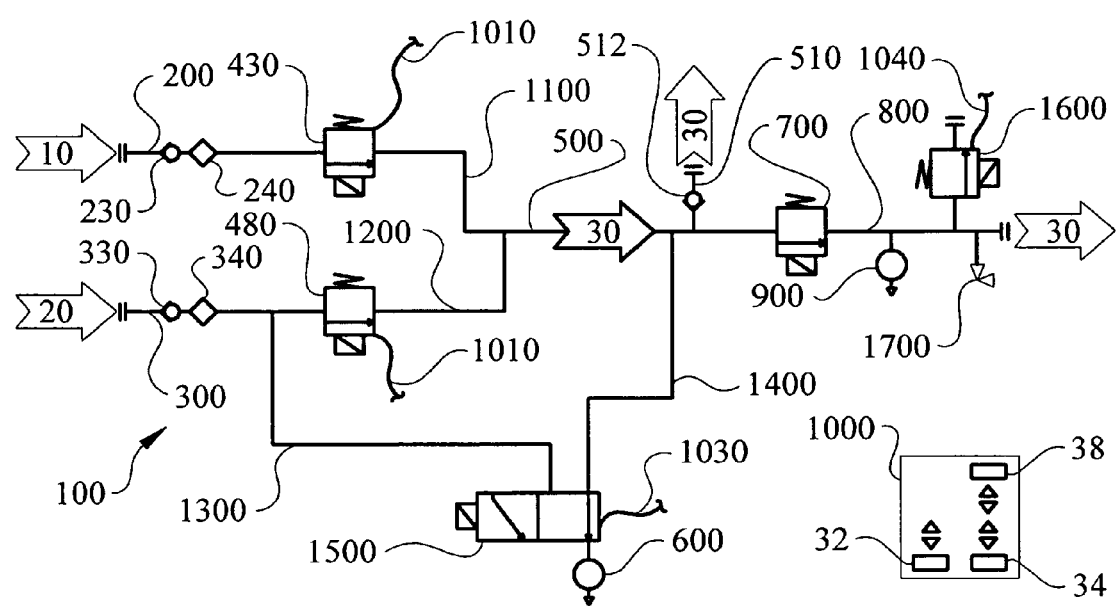
FIG. 7 is a schematic of the present invention, not to scale.

The present invention may also incorporate a calibration valve (1500) to control which gas (10, 20, 30) is sensed by the gas sensor (600), as seen in FIGS. 5 and 7. Incorporation of the calibration valve (1500) allows the gas blender (100) to verify that the gas sensor (600) is properly functioning. For example, in one of the healthcare examples above, the gas sensor (600) is an oxygen sensor. Here, the gas blender (100) is connected to a source of 100% oxygen. Therefore, by directing 100% oxygen to the gas sensor (600) via the calibration valve (1500), the gas blender (100) can test the gas sensor (600) to see if it produces a reading of 100% oxygen. The calibration valve (1500) is most commonly a 3-way 2-position solenoid valve. In other words, the calibration valve (1500) has two inputs and one output and the valve merely directs which input is blocked-off and which input gets to flow freely to the output.

This embodiment incorporates a secondary gas calibration passageway (1300), a mixed gas measurement passageway (1400), and the calibration valve (1500). The secondary gas calibration passageway (1300) is in fluid communication with the secondary gas inlet passageway (300). The mixed gas measurement passageway (1400) is in fluid communication with the mixed gas distribution passageway (500). The calibration valve (1500) directs gas flow from either the secondary gas calibration passageway (1300) or the mixed gas measurement passageway (1400) to the gas sensor (600) at the direction of a calibration signal (1030) generated by the controller (1000). The controller (1000) may generate the calibration signal (1030) upon the occurrence of any number of events. For example, the controller (1000) may generate the calibration signal (1030), and thus test the gas sensor (600), every time operation of the gas blender (100) is initiated, or after a specified period of operation, which could be hours of operation, number of cycles, etc. Further, the controller (1000) may prevent operation of the gas blender (100) if the gas signal (610) generated by the gas sensor (600) does not accurately identify the secondary gas (20).

The present invention may also incorporate a mixed gas vent valve (1600) in fluid communication with the mixed gas controlled passageway (800), as seen in FIG. 7. The mixed gas vent valve (1600) vents mixed gas (30) from the mixed gas controlled passageway (800) in response to a vent control signal (1040) generated by the controller (1000). The vent control signal (1040) is generated by comparing a predetermined mixed gas vent setpoint (38) and the delivery sensing signal (910). The predetermined mixed gas vent setpoint (38) is essentially an over pressure safety setting. With reference again to a CPAP application, the predetermined mixed gas vent setpoint (38) is generally around 12 centimeters of water. In one embodiment the mixed gas vent valve (1600) is a 2-way solenoid valve that simply opens when the delivery sensor (900) senses a pressure in the mixed gas controlled passageway (800) that is greater than the predetermined mixed gas vent setpoint (38), thereby venting mixed gas (30) from the mixed gas controlled passageway (800), and simply closes when the pressure in the mixed gas controlled passageway (800) drops below the predetermined mixed gas vent setpoint (38).

The present invention may further incorporate a relief valve (1700) in fluid communication with the mixed gas controlled passageway (800). The relief valve (1700) relieves mixed gas (30) from the mixed gas controlled passageway (800) if the pressure of the mixed gas (30) in the mixed gas controlled passageway (800) exceeds a predetermined mixed gas relief setpoint (40). The predetermined mixed gas relief setpoint (40) is generally significantly higher then the predetermined mixed gas vent setpoint (38). In fact, in the CPAP application example used throughout this section the predetermined mixed gas relief setpoint (40) is approximately 210 centimeters of water. In this embodiment the relief valve (1700) is an automatic mechanical relief valve.

As one with skill in the art will appreciate, the various inlets and outlets of the gas blender (100) may incorporate check valves to limit the flow of the gas to a particular direction. Such check valves may be in fluid communication with the various inlets and outlets and external to the gas blender (100), or the check valves may be part of the gas blender (100). Therefore, one embodiment of the gas blender (100) includes a primary gas check valve (230) in the primary gas inlet passageway (200), a secondary gas check valve (330) in the secondary gas inlet passageway (300), and an auxiliary mixed gas outlet check valve (512) in the auxiliary mixed gas outlet (510), as seen in FIG. 7. Additionally, one with skill in the art will appreciate that numerous filters may be incorporated into the gas blender (100), such as the primary gas filter (240) and the secondary gas filter (340), also seen in FIG. 7. The filters (240, 340) are generally 5-50 micron filters and may incorporate a water trap, particularly on the primary gas (10) side of the gas blender (100) when the primary gas (10) is compressed air.

Figure 8:
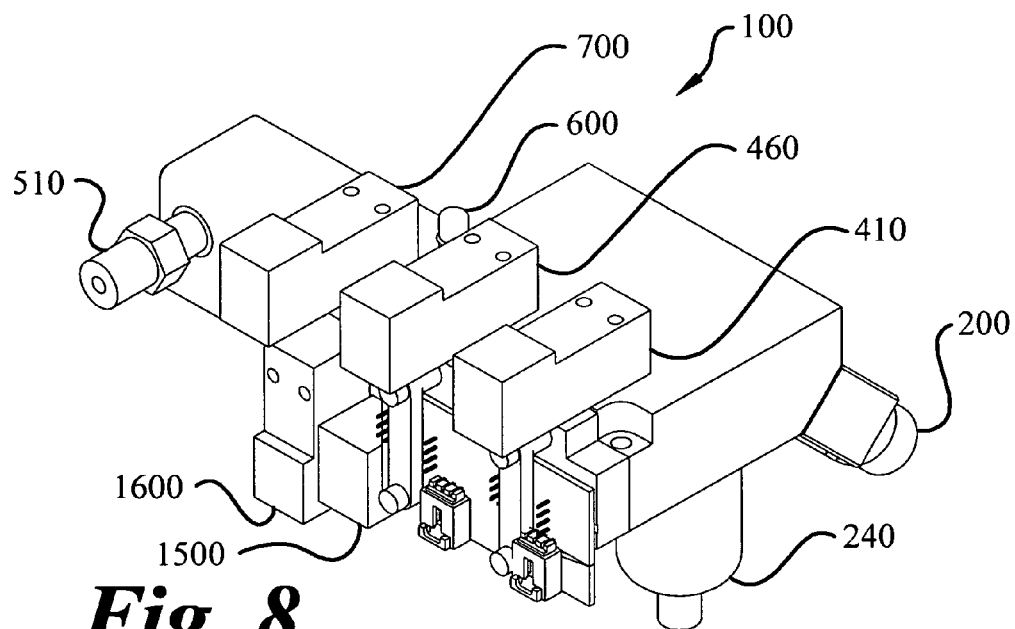
FIG. 8 is an elevated perspective view of the present invention, not to scale.
Figure 9:
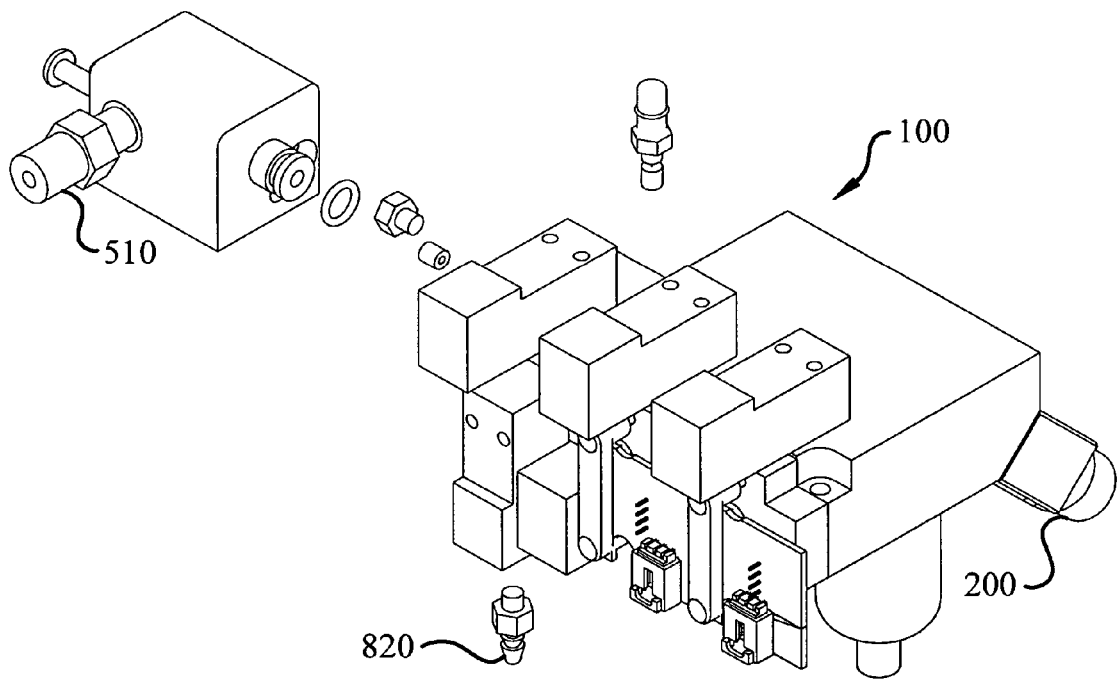
FIG. 9 is an exploded assembly view of several components of the embodiment of FIG. 8, not to scale.
Figure 10:
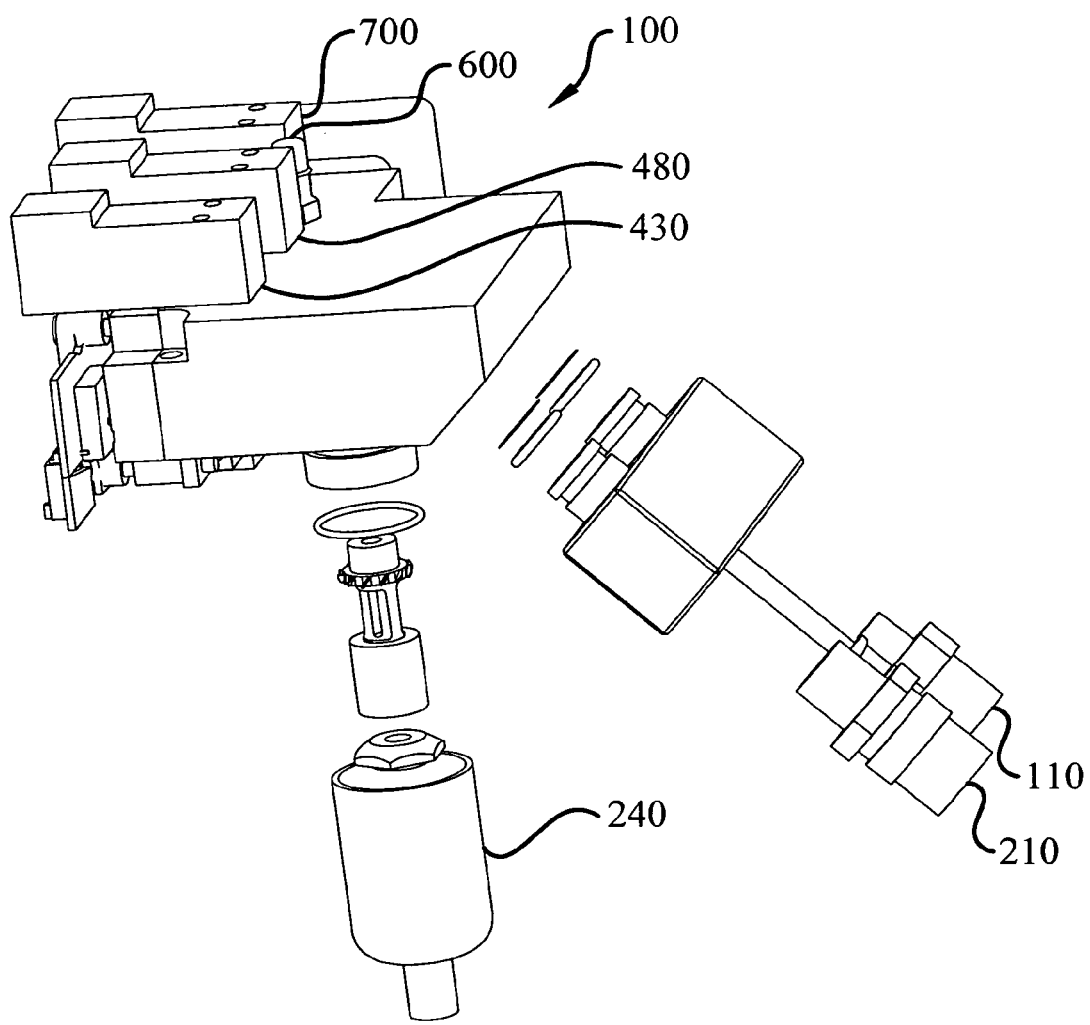
FIG. 10 is an exploded assembly view of several components of the embodiment of FIG. 8, not to scale.

One particular embodiment is illustrated in FIGS. 8-15. These figures correspond generally to the schematic diagram of FIG. 7. The gas blender (100) seen in FIG. 8, illustrates the location of the various valves of this embodiment, namely the primary gas control valve (410), the secondary gas control valve (460), the mixed gas delivery control valve (700), the calibration valve (1500), and the mixed gas vent valve (1600). The auxiliary mixed gas outlet (510) is also seen in FIG. 8. The gas blender (100) of FIG. 8 is seen in assembly view in FIG. 9. The mixed gas controlled passageway (800), and thus, the mixed gas controlled passageway outlet (820), which is generally considered the outlet that serves the patient, leaves the gas blender (100) from the bottom, as seen in FIGS. 9 and 13. The two inlet connections, namely the primary gas inlet port (210) and the secondary gas inlet port (310) are best illustrated in FIG. 10, as is the gas sensor (600).

The gas passageways of the present embodiment are best illustrated by referencing the top plan view of FIG. 11 and the associated sections of FIGS. 12-15. For example, one can follow the primary gas (10) flow route by observing the primary gas inlet port (210) in FIG. 11, and referencing the section of FIG. 14 taken along section line 14-14 in FIG. 11.

The primary gas (10) enters the primary gas inlet port (210) and is then directed through the primary gas filter (240), not seen in FIGS. 11-15 but shown in FIGS. 8 and 10. The primary gas (10) is then routed to a chamber that contains the primary gas check valve (230), not shown for clarity, and exits the main body of the gas blender (100) to enter the primary gas control valve (410), shown schematically in FIGS. 14 and 15. The primary gas (10) is then directed back into the main body of the gas blender (100) via the primary gas controlled passageway (1100), seen in FIG. 15, which connects to the mixed gas distribution passageway (500). The mixed gas distribution passageway (500) runs almost the entire length of the gas blender (100), as seen in FIG. 11, and has section line 15-15 cut down the middle of the passageway (500), with the section shown in FIG. 15.

Further, one can also follow the secondary gas (20) flow route by first referencing FIG. 11. The secondary gas (20) enters the gas blender (100) via the secondary gas inlet port (310) and flows through the secondary gas inlet passageway (300) that connects to a chamber that contains the secondary gas check valve (330), not shown for clarity. While a section is not cut through the secondary gas inlet passageway (300), as section 14-14 cuts through the primary gas inlet passageway (200), the route is approximately the same, except that the secondary gas inlet passageway (300) does not contain a large water trap filter as seen in the primary gas inlet passageway (200), because in this design the secondary gas (20) is oxygen that has been previously filtered. Similar to the primary gas (10) route, the secondary gas (20) leaves the main body of the gas blender (100) out the top, to enter the secondary gas control valve (460), seen in FIG. 8. The secondary gas (20) then returns the main body of the gas blender (100) through the secondary gas controlled passage (1200), as seen in FIG. 15, which connects to the mixed gas distribution passageway (500).

The mixed gas (30) then proceeds down the mixed gas distribution passageway (500) until it reaches the point of section line 13-13 of FIG. 11. Section line 13-13 is the point at which the mixed gas delivery valve (700) connects to the mixed gas distribution passageway (500), as seen in FIG. 13. The mixed gas (30) exits the main body of the gas blender (100), proceeds through the mixed gas delivery valve (700), and returns to the main body of the gas blender (100) via the mixed gas controlled passageway (800), also seen in FIG. 13. The mixed gas (30), now at the predetermined mixture setpoint (32) and the predetermined control setpoint, leaves the gas blender (100) out of the bottom.

With reference again to FIG. 11, the mixed gas distribution passageway (500) extends beyond section line 13-13 to the auxiliary mixed gas outlet (510), shown literally in FIG. 9 and schematically in FIG. 15. Along the route of the mixed gas (30) down the mixed gas distribution passageway (500) to the mixed gas delivery control valve (700) at section line 13-13, the mixed gas (30) passes section line 12-12 which is the point at which the calibration valve (1500) communicates with the mixed gas distribution passageway (500). The calibration valve (1500) draws mixed gas (30) from the mixed gas distribution passageway (500) via the mixed gas measurement passageway (1400), and draws secondary gas (20) from the secondary gas inlet passageway (300) via the secondary gas calibration passageway (1300), as seen in FIG. 12. The discharge from the calibration valve (1500) is then routed to the gas sensor (600).

Additionally, the mixed gas (30) passes the location of the mixed gas vent valve (1600) along the path out of the mixed gas controlled passageway (800), as seen in FIG. 13. The mixed gas vent valve (1600) is seen on the front of the gas blender (100) in FIG. 8, and the connection to the mixed gas controlled passageway (800) is seen in FIG. 13.

Numerous alterations, modifications, and variations of the preferred embodiments disclosed herein will be apparent to those skilled in the art and they are all anticipated and contemplated to be within the spirit and scope of the instant invention. For example, although specific embodiments have been described in detail, those with skill in the art will understand that the preceding embodiments and variations can be modified to incorporate various types of substitute and or additional or alternative materials, relative arrangement of elements, and dimensional configurations. Accordingly, even though only few variations of the present invention are described herein, it is to be understood that the practice of such additional modifications and variations and the equivalents thereof, are within the spirit and scope of the invention as defined in the following claims.

INDUSTRIAL APPLICABILITY

A gas blender with auxiliary mixed gas outlet answers a long felt need for a Continuous Positive Airway Pressure (CPAP) device gas blender capable of supplying mixed gas to external, non-CPAP, equipment. The incorporation of an auxiliary mixed gas source outlet capable of supplying mixed gas to auxiliary equipment at a relatively high flow rate and a pressure significantly greater than the final controlled mixed gas pressure permits the elimination of external gas blenders commonly required for auxiliary equipment, such as a nebulizers or resuscitation bags.

We claim:

1. A gas blender with source pressure auxiliary mixed gas outlet (100) for mixing a primary gas (10), at a primary gas source pressure, and a secondary gas (20), at a secondary gas source pressure, in a controlled manner to produce a mixed gas (30) having a predetermined mixture setpoint (32) and a predetermined control setpoint (34), and providing a mixed gas (30) source having a pressure of at least fifty percent of the first gas source pressure for selective use by at least one auxiliary piece of equipment, comprising:

a primary gas inlet passageway (200) having a primary gas inlet port (210), for receiving the primary gas (10) from an external source, and a primary gas inlet passageway discharge (220);

a secondary gas inlet passageway (300) having a secondary gas inlet port (310), for receiving the secondary gas (20) from an external source, and a secondary gas inlet passageway discharge (320);

a gas mixing apparatus (400) in fluid communication with the primary gas inlet passageway (200), the secondary gas inlet passageway (300), and a mixed gas distribution passageway (500), wherein the gas mixing apparatus (400) receives primary gas (10) through the primary gas inlet passageway (200) and receives secondary gas (20) through the secondary gas inlet passageway (300), wherein the gas mixing apparatus (400) mixes the primary gas (10) with the secondary gas (20) in response to a mixing control signal (1010) thereby producing the mixed gas (30) at the predetermined mixture setpoint (32) and a pressure of at least fifty percent of the primary gas source pressure that then exits the gas mixing apparatus (400) via the mixed gas distribution passageway (500), wherein the mixed gas distribution passageway (500) has an auxiliary mixed gas outlet (510) for supplying the mixed gas (30) at the predetermined mixture setpoint (32) and a pressure of at least fifty percent of the primary gas source pressure for use by the at least one auxiliary piece of equipment, wherein the at least one auxiliary piece of equipment comprises one of a nebulizer and a resuscitation bag;

a gas sensor (600) in fluid communication with the mixed gas distribution passageway (500) for producing a gas signal (610);

a mixed gas delivery control valve (700) in fluid communication with the mixed gas distribution passageway (500) and a mixed gas controlled passageway (800), wherein the mixed gas delivery control valve (700) receives the mixed gas (30) at the predetermined mixture setpoint (32) and modulates in response to a delivery control signal (1020) thereby fixing the mixed gas (30) at the predetermined mixture setpoint (32) and the predetermined control setpoint (34) that then exits the mixed gas delivery control valve (700) via the mixed gas controlled passageway (800) at a mixed gas controlled passageway discharge (820) separate from the auxiliary mixed gas outlet (510);

a delivery sensor (900) in fluid communication with the mixed gas (30) after it exits the mixed gas delivery control valve (700) for generating a delivery sensing signal (910); and a controller (1000) for comparing the predetermined mixture setpoint (32) and the gas signal (610), and generating the mixing control signal (1010), and for comparing the predetermined control setpoint (34) and the delivery sensing signal (910), and generating the delivery control signal (1020).

2. The gas blender (100) of claim 1, wherein the gas mixing apparatus (400) includes a primary gas control valve (410) and a secondary gas control valve (460).

3. The gas blender (100) of claim 2, wherein the primary gas control valve (410) is a primary gas proportional solenoid valve (420) and the secondary gas control valve (460) is a secondary gas proportional solenoid valve (470).

4. The gas blender (100) of claim 3, wherein the primary gas proportional solenoid valve (420) is a 2-way primary gas proportional solenoid valve (430) and the secondary gas proportional solenoid valve (470) is a 2-way secondary gas proportional solenoid valve (480), wherein the 2-way primary gas proportional solenoid valve (430) is in fluid communication with the primary gas inlet passageway (200) and a primary gas controlled passageway (1100) such that the 2-way primary gas proportional solenoid valve (430) receives the primary gas (10) from the primary gas inlet passageway (200), modulates in response to the mixing control signal (1010), and discharges the modulated primary gas (10) to the primary gas controlled passageway (1100) that is in fluid communication with the mixed gas distribution passageway (500), and wherein the 2-way secondary gas proportional solenoid valve (480) is in fluid communication with the secondary gas inlet passageway (300) and a secondary gas controlled passageway (1200) such that the 2-way secondary gas proportional solenoid valve (480) receives the secondary gas (20) from the secondary gas inlet passageway (300), modulates in response to the mixing control signal (1010), and discharges the modulated secondary gas (20) to the secondary gas controlled passageway (1200) that is in fluid communication with the mixed gas distribution passageway (500), such that the modulated primary gas (10) and the modulated secondary gas (20) mix in the mixed gas distribution passageway (500) to achieve the predetermined mixture setpoint (32).

5. The gas blender (100) of claim 3, wherein the primary gas proportional solenoid valve (420) is a 2-way primary gas proportional solenoid valve (430) and the secondary gas proportional solenoid valve (470) is a 3-way secondary gas proportional solenoid valve (490), wherein the 2-way primary gas proportional solenoid valve (430) is in fluid communication with the primary gas inlet passageway (200) and a primary gas controlled passageway (1100) such that the 2-way primary gas proportional solenoid valve (430) receives the primary gas (10) from the primary gas inlet passageway (200), modulates in response to the mixing control signal (1010) only when the predetermined mixture setpoint (32) is at or above a predetermined high concentration setpoint (36) otherwise the 2-way primary gas proportional solenoid valve (430) is fully open, and discharges the primary gas (10) to the primary gas controlled passageway (1100) that is in fluid communication with the 3-way secondary gas proportional solenoid valve (490), and wherein the 3-way secondary gas proportional solenoid valve (490) is in fluid communication with the secondary gas inlet passageway (300), the primary gas controlled passageway (1100), and the mixed gas distribution passageway (500) such that the 3-way secondary gas proportional solenoid valve (430) receives the secondary gas (20) from the secondary gas inlet passageway (300) and receives the primary gas (10) from the primary gas controlled passageway (1100), modulates in response to the mixing control signal (1010), and discharges the mixed gas (30) to the mixed gas distribution passageway (500) at the predetermined mixture setpoint (32).

6. The gas blender (100) of claim 5, wherein the primary gas (10) is compressed air, the secondary gas (20) is oxygen, and the predetermined high concentration setpoint (36) of the mixed gas (30) is substantially sixty percent oxygen.

7. The gas blender (100) of claim 3, wherein the primary gas proportional solenoid valve (420) is a 3-way primary gas proportional solenoid valve (440) and the secondary gas proportional solenoid valve (470) is a 2-way secondary gas proportional solenoid valve (480), wherein the 2-way secondary gas proportional solenoid valve (480) is in fluid communication with the secondary gas inlet passageway (300) and a secondary gas controlled passageway (1200) such that the 2-way secondary gas proportional solenoid valve (480) receives the secondary gas (20) from the secondary gas inlet passageway (300), modulates in response to the mixing control signal (1010) only when the predetermined mixture setpoint (32) is at or above a predetermined high concentration setpoint (36), otherwise the 2-way secondary gas proportional solenoid valve (480) is fully open, and discharges the secondary gas (20) to the secondary gas controlled passageway (1200) that is in fluid communication with the 3-way primary gas proportional solenoid valve (440), and wherein the 3-way primary gas proportional solenoid valve (440) is in fluid communication with the primary gas inlet passageway (200), the secondary gas controlled passageway (1200), and the mixed gas distribution passageway (500) such that the 3-way primary gas proportional solenoid valve (440) receives the primary gas (10) from the primary gas inlet passageway (200) and receives the secondary gas (20) from the secondary gas controlled passageway (1200), modulates in response to the mixing control signal (1010), and discharges the mixed gas (30) to the mixed gas distribution passageway (500) at the predetermined mixture setpoint (32).

8. The gas blender (100) of claim 1, further including a secondary gas calibration passageway (1300), a mixed gas measurement passageway (1400), and a calibration valve (1500), wherein the secondary gas calibration passageway (1300) is in fluid communication with the secondary gas inlet passageway (300), the mixed gas measurement passageway (1400) is in fluid communication with the mixed gas distribution passageway (500), and the calibration valve (1500) directs gas flow from either the secondary gas calibration passageway (1300) or the mixed gas measurement passageway (1400) to the gas sensor (600) at the direction of a calibration signal (1030) generated by the controller (1000).

9. The gas blender (100) of claim 8, wherein the controller (1000) generates a calibration signal (1030) commanding the calibration valve (1500) to open the secondary gas calibration passageway (1300) to the gas sensor (600) for a predetermined period at the start of each use of the gas blender (100), and the controller (1000) prevents operation of the gas blender (100) if the calibration signal (1030) does not represent substantially all secondary gas (30).

10. The gas blender (100) of claim 1, wherein the delivery sensor (900) is a pressure sensor (920) and the predetermined control setpoint (34) is an adjustable mixed gas delivery pressure desired in the mixed gas controlled passageway (800).

11. The gas blender (100) of claim 1, wherein the delivery sensor (900) is a flow sensor (930) and the predetermined control setpoint (34) is an adjustable mixed gas flow rate desired in the mixed gas controlled passageway (800).

12. The gas blender (100) of claim 1, further including a mixed gas vent valve (1600) in fluid communication with the mixed gas controlled passageway (800), wherein the mixed gas vent valve (1600) vents mixed gas (30) from the mixed gas controlled passageway (800) in response to a vent control signal (1040) generated by the controller (1000) by comparing a predetermined mixed gas vent setpoint (38) and the delivery sensing signal (910).

13. The gas blender (100) of claim 12, wherein the predetermined mixed gas vent setpoint (38) is 12 centimeters of water.

14. The gas blender (100) of claim 1, further including a relief valve (1700) in fluid communication with the mixed gas controlled passageway (800), wherein the relief valve (1700) relieves mixed gas (30) from the mixed gas controlled passageway (800) if the pressure of the mixed gas (30) in the mixed gas controlled passageway (800) exceeds a predetermined mixed gas relief setpoint (40).

15. The gas blender (100) of claim 14, wherein the predetermined mixed gas relief setpoint (40) is 210 centimeters of water.

16. The gas blender (100) of claim 1, further including a primary gas check valve (230) in the primary gas inlet passageway (200), a secondary gas check valve (330) in the secondary gas inlet passageway (300), and an auxiliary mixed gas outlet check valve (512) in the auxiliary mixed gas outlet (510).

17. The gas blender (100) of claim 1, wherein the auxiliary mixed gas outlet (510) is positioned between the mixed gas distribution passageway (500) and the mixed gas delivery control valve (700).

18. A gas blender with source pressure auxiliary mixed gas outlet (100) for mixing a primary gas (10), at a primary gas source pressure, and a secondary gas (20), at a secondary gas source pressure, in a controlled manner to produce a mixed gas (30) having a predetermined mixture setpoint (32) and a predetermined control setpoint (34), and providing a mixed gas (30) source at a pressure of at least fifty percent of the first gas source pressure for selective use by at least one auxiliary piece of equipment, comprising:

a primary gas inlet passageway (200) having a primary gas inlet port (210), for receiving the primary gas (10) from an external source, and a primary gas inlet passageway discharge (220);

a secondary gas inlet passageway (300) having a secondary gas inlet port (310), for receiving the secondary gas (20) from an external source, and a secondary gas inlet passageway discharge (320);

a gas mixing apparatus (400), including a primary gas control valve (410) and a secondary gas control valve (460), in fluid communication with the primary gas inlet passageway (200), the secondary gas inlet passageway (300), and a mixed gas distribution passageway (500), wherein the primary gas control valve (410) receives primary gas (10) through the primary gas inlet passageway (200) and the secondary gas control valve (460) receives secondary gas (20) through the secondary gas inlet passageway (300), wherein the primary gas control valve (410) is a 2-way primary gas proportional solenoid valve (430) and the secondary gas control valve (460) is a 2-way secondary gas proportional solenoid valve (480), wherein the 2-way primary gas proportional solenoid valve (430) is in fluid communication with the primary gas inlet passageway (200) and a primary gas controlled passageway (1100) such that the 2-way primary gas proportional solenoid valve (430) receives the primary gas (10) from the primary gas inlet passageway (200), modulates in response to a mixing control signal (1010), and discharges the modulated primary gas (10) to the primary gas controlled passageway (1100) that is in fluid communication with the mixed gas distribution passageway (500), and wherein the 2-way secondary gas proportional solenoid valve (480) is in fluid communication with the secondary gas inlet passageway (300) and a secondary gas controlled passageway (1200) such that the 2-way secondary gas proportional solenoid valve (480) receives the secondary gas (20) from the secondary gas inlet passageway (300), modulates in response to the mixing control signal (1010), and discharges the modulated secondary gas (20) to the secondary gas controlled passageway (1200) that is in fluid communication with the mixed gas distribution passageway (500), such that the modulated primary gas (10) and the modulated secondary gas (20) mix in the mixed gas distribution passageway (500) to achieve the predetermined mixture setpoint (32), and wherein the mixed gas distribution passageway (500) has an auxiliary mixed gas outlet (510) for supplying the mixed gas (30) at the predetermined mixture setpoint (32) and a pressure of at least fifty percent of the primary gas source pressure for use by the at least one auxiliary piece of equipment, wherein the at least one auxiliary piece of equipment comprises one of a nebulizer and a resuscitation bag;

a gas sensor (600) in fluid communication with the mixed gas distribution passageway (500) for producing a gas signal (610);

a mixed gas delivery control valve (700) in fluid communication with the mixed gas distribution passageway (500) and a mixed gas controlled passageway (800), wherein the mixed gas delivery control valve (700) receives the mixed gas (30) at the predetermined mixture setpoint (32) and modulates in response to a delivery control signal (1020) thereby fixing the mixed gas (30) at the predetermined mixture setpoint (32) and the predetermined control setpoint (34) that then exits the mixed gas delivery control valve (700) via the mixed gas controlled passageway (800) at a mixed gas controlled passageway discharge (820) separate from the auxiliary mixed gas outlet (510);

a delivery sensor (900) in fluid communication with the mixed gas (30) after it exits the mixed gas delivery control valve (700) for generating a delivery sensing signal (910); and a controller (1000) for comparing the predetermined mixture setpoint (32) and the gas signal (610), and generating the mixing control signal (1010), and for comparing the predetermined control setpoint (34) and the delivery sensing signal (910), and generating the delivery control signal (1020).

19. The gas blender (100) of claim 18, further including a secondary gas calibration passageway (1300), a mixed gas measurement passageway (1400), and a calibration valve (1500), wherein the secondary gas calibration passageway (1300) is in fluid communication with the secondary gas inlet passageway (300), the mixed gas measurement passageway (1400) is in fluid communication with the mixed gas distribution passageway (500), and the calibration valve (1500) directs gas flow from either the secondary gas calibration passageway (1300) or the mixed gas measurement passageway (1400) to the gas sensor (600) at the direction of a calibration signal (1030) generated by the controller (1000).

20. The gas blender (100) of claim 19, wherein the controller (1000) generates a calibration signal (1030) commanding the calibration valve (1500) to open the secondary gas calibration passageway (1300) to the gas sensor (600) for a predetermined period at the start of each use of the gas blender (100), and the controller (1000) prevents operation of the gas blender (100) if the calibration signal (1030) does not represent substantially all secondary gas (30).

21. The gas blender (100) of claim 18, wherein the delivery sensor (900) is a flow sensor (930) and the predetermined control setpoint (34) is an adjustable mixed gas flow rate desired in the mixed gas controlled passageway (800).

22. The gas blender (100) of claim 18, further including a mixed gas vent valve (1600) in fluid communication with the mixed gas controlled passageway (800), wherein the mixed gas vent valve (1600) vents mixed gas (30) from the mixed gas controlled passageway (800) in response to a vent control signal (1040) generated by the controller (1000) by comparing a predetermined mixed gas vent setpoint (38) and the delivery sensing signal (910).

23. The gas blender (100) of claim 18, wherein the predetermined mixed gas vent setpoint (38) is 12 centimeters of water.

24. The gas blender (100) of claim 18, further including a relief valve (1700) in fluid communication with the mixed gas controlled passageway (800), wherein the relief valve (1700) relieves mixed gas (30) from the mixed gas controlled passageway (800) if the pressure of the mixed gas (30) in the mixed gas controlled passageway (800) exceeds a predetermined mixed gas relief setpoint (40).

25. The gas blender (100) of claim 24, wherein the predetermined mixed gas relief setpoint (40) is 210 centimeters of water.

26. The gas blender (100) of claim 18, further including a primary gas check valve (230) in the primary gas inlet passageway (200), a secondary gas check valve (330) in the secondary gas inlet passageway (300), and an auxiliary mixed gas outlet check valve (512) in the auxiliary mixed gas outlet (510).

27. The gas blender (100) of claim 18, wherein the delivery sensor (900) is a pressure sensor (920) and the predetermined control setpoint (34) is an adjustable mixed gas delivery pressure desired in the mixed gas controlled passageway (800).

28. A gas blender with source pressure auxiliary mixed gas outlet (100) for mixing a primary gas (10), at a primary gas source pressure, and a secondary gas (20), at a secondary gas source pressure, in a controlled manner to produce a mixed gas (30) having a predetermined mixture setpoint (32) and a predetermined control setpoint (34), and providing a mixed gas (30) source at a pressure of at least fifty percent of the first gas source pressure for selective use by at least one auxiliary piece of equipment, comprising:

a primary gas inlet passageway (200) having a primary gas inlet port (210), for receiving the primary gas (10) from an external source, and a primary gas inlet passageway discharge (220);

a secondary gas inlet passageway (300) having a secondary gas inlet port (310), for receiving the secondary gas (20) from an external source, and a secondary gas inlet passageway discharge (320);

a gas mixing apparatus (400), including a primary gas control valve (410) and a secondary gas control valve (460), in fluid communication with the primary gas inlet passageway (200), the secondary gas inlet passageway (300), and a mixed gas distribution passageway (500), wherein the primary gas control valve (410) is a 2-way primary gas proportional solenoid valve (430) and the secondary gas control valve (460) is a 3-way secondary gas proportional solenoid valve (490), wherein the 2-way primary gas proportional solenoid valve (430) is in fluid communication with the primary gas inlet passageway (200) and a primary gas controlled passageway (1100) such that the 2-way primary gas proportional solenoid valve (430) received the primary gas (10) from the primary gas inlet passageway (200), modulates in response to a mixing control signal (1010) only when the predetermined mixture setpoint (32) is at or above a predetermined high concentration setpoint (36), otherwise the 2-way primary gas proportional solenoid valve (430) is fully open, and discharges the primary gas (10) to the primary gas controlled passageway (1100) that is in fluid communication with the 3-way secondary gas proportional solenoid valve (490), and wherein the 3-way secondary gas proportional solenoid valve (490) is in fluid communication with the secondary gas inlet passageway (300), the primary gas controlled passageway (1100), and the mixed gas distribution passageway (500) such that the 3-way secondary gas proportional solenoid valve (430) receives the secondary gas (20) from the secondary gas inlet passageway (300) and receives the primary gas (10) from the primary gas controlled passageway (1100), modulates in response to the mixing control signal (1010), and discharges the mixed gas (30) to the mixed gas distribution passageway (500) at the predetermined mixture setpoint (32), wherein the mixed gas distribution passageway (500) has an auxiliary mixed gas outlet (510) for supplying the mixed gas (30) at the predetermined mixture setpoint (32) and a pressure of at least fifty percent of the primary gas source pressure for use by the at least one auxiliary piece of equipment, wherein the at least one auxiliary piece of equipment comprises one of a nebulizer and a resuscitation bag;

a gas sensor (600) in fluid communication with the mixed gas distribution passageway (500) for producing a gas signal (610);

a mixed gas delivery control valve (700) in fluid communication with the mixed gas distribution passageway (500) and a mixed gas controlled passageway (800), wherein the mixed gas delivery control valve (700) receives the mixed gas (30) at the predetermined mixture setpoint (32) and modulates in response to a delivery control signal (1020) thereby fixing the mixed gas (30) at the predetermined mixture setpoint (32) and the predetermined control setpoint (34) that then exits the mixed gas delivery control valve (700) via the mixed gas controlled passageway (800) at a mixed gas controlled passageway discharge (820) separate from the auxiliary mixed gas outlet (510);

a delivery sensor (900) in fluid communication with the mixed gas (30) after it exits the mixed gas delivery control valve (700) for generating a delivery sensing signal (910); and a controller (1000) for comparing the predetermined mixture setpoint (32) and the gas signal (610), and generating the mixing control signal (1010), and for comparing the predetermined control setpoint (34) and the delivery sensing signal (910), and generating the delivery control signal (1020).

29. The gas blender (100) of claim 28, further including a secondary gas calibration passageway (1300), a mixed gas measurement passageway (1400), and a calibration valve (1500), wherein the secondary gas calibration passageway (1300) is in fluid communication with the secondary gas inlet passageway (300), the mixed gas measurement passageway (1400) is in fluid communication with the mixed gas distribution passageway (500), and the calibration valve (1500) directs gas flow from either the secondary gas calibration passageway (1300) or the mixed gas measurement passageway (1400) to the gas sensor (600) at the direction of a calibration signal (1030) generated by the controller (1000).

30. The gas blender (100) of claim 29, wherein the controller (1000) generates a calibration signal (1030) commanding the calibration valve (1500) to open the secondary gas calibration passageway (1300) to the gas sensor (600) for a predetermined period at the start of each use of the gas blender (100), and the controller (1000) prevents operation of the gas blender (100) if the calibration signal (1030) does not represent substantially all secondary gas (30).

31. The gas blender (100) of claim 28, wherein the delivery sensor (900) is a pressure sensor (920) and the predetermined control setpoint (34) is an adjustable mixed gas delivery pressure desired in the mixed gas controlled passageway (800).

32. The gas blender (100) of claim 28, wherein the delivery sensor (900) is a flow sensor (930) and the predetermined control setpoint (34) is an adjustable mixed gas flow rate desired in the mixed gas controlled passageway (800).

33. The gas blender (100) of claim 28, further including a mixed gas vent valve (1600) in fluid communication with the mixed gas controlled passageway (800), wherein the mixed gas vent valve (1600) vents mixed gas (30) from the mixed gas controlled passageway (800) in response to a vent control signal (1040) generated by the controller (1000) by comparing a predetermined mixed gas vent setpoint (38) and the delivery sensing signal (910).

34. The gas blender (100) of claim 28, wherein the predetermined mixed gas vent setpoint (38) is 12 centimeters of water.

35. The gas blender (100) of claim 28, wherein the primary gas (10) is compressed air, the secondary gas (20) is oxygen, and the predetermined high concentration setpoint (36) of the mixed gas (30) is substantially sixty percent oxygen.

* * * * *

UNITED STATES PATENT AND TRADEMARK OFFICE
CERTIFICATE OF CORRECTION

| | | |
|---|---|---|
| PATENT NO. | : 8,006,692 B2 | |
| APPLICATION NO. | : 11/292641 | |
| DATED | : August 30, 2011 | |
| INVENTOR(S) | : Smith et al. | |

It is certified that error appears in the above-identified patent and that said Letters Patent is hereby corrected as shown below:

Column 10, line 21, delete "then" and insert in place thereof --than--.

Signed and Sealed this
Twenty-ninth Day of November, 2011

David J. Kappos
*Director of the United States Patent and Trademark Office*